(12) United States Patent
Barlag et al.

(10) Patent No.: US 8,128,803 B2
(45) Date of Patent: Mar. 6, 2012

(54) METHOD AND SYSTEM FOR DETERMINING THE CONCENTRATION OF AN ANALYTE/ENZYME COMPLEX OR OF AN ANALYTE/ENZYME CONJUGATE, ESPECIALLY FOR THE ELECTROCHEMICAL DETECTION OF THE ANALYTE, AND CORRESPONDING MEASURING DEVICE

(75) Inventors: Heike Barlag, Nürnberg (DE); Walter Gumbrecht, Herzogenaurach (DE); Konrad Mund, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 1067 days.

(21) Appl. No.: 11/989,938

(22) PCT Filed: Jul. 31, 2006

(86) PCT No.: PCT/EP2006/064842
§ 371 (c)(1),
(2), (4) Date: Feb. 4, 2008

(87) PCT Pub. No.: WO2007/014931
PCT Pub. Date: Feb. 8, 2007

(65) Prior Publication Data
US 2010/0155263 A1    Jun. 24, 2010

(30) Foreign Application Priority Data

Aug. 4, 2005 (DE) .......................... 10 2005 037 436

(51) Int. Cl.
*G01N 33/543* (2006.01)
*G01N 27/26* (2006.01)
*G01N 27/49* (2006.01)
(52) U.S. Cl. ................ 205/777.5; 204/403.14; 435/817; 435/6.1; 435/25; 435/287.2

(58) Field of Classification Search ..... 204/400–403.15, 204/406; 435/6; 205/775, 777.5, 793.5; 436/6.1, 287.2, 25, 817
See application file for complete search history.

(56) References Cited

U.S. PATENT DOCUMENTS
6,682,648 B1 * 1/2004 MacPhee et al. .......... 205/777.5
(Continued)

FOREIGN PATENT DOCUMENTS
DE      43 35 241       4/1995
(Continued)

OTHER PUBLICATIONS

H. Gunasingham et al. "Pulsed Amperometric Detection of Glucose Using a Mediated Enzyme Electrode" Journal of Electroanalytical Chemistry 287, 1990; pp. 234-362.

(Continued)

*Primary Examiner* — Jeffrey T Barton
*Assistant Examiner* — Jennifer Dieterle
(74) *Attorney, Agent, or Firm* — Staas & Halsey LLP

(57) ABSTRACT

A method follow the change in concentration of a redox-active substance, whereby suitable potentials for a reduction process or an oxidation process are applied to the working electrode of a measuring device. The potential of the working electrode is pulsed and measuring phases and relaxation phases are alternately produced, the pulse lengths of measuring phase and relaxation phase being determined in a suitable manner. A rapid relaxation of the concentration gradient is electrochemically forced so that the measurement can be carried out on simple transducer arrays. A device for carrying out the method includes a transducer array in addition to a suitable potentiostat. The transducer array can be formed of a planar metal substrate on which at least one flexible insulator is disposed, the metal surface and the insulator surface being firmly linked. The transducer array can also be formed of silicone-based CMOS structures.

16 Claims, 10 Drawing Sheets

U.S. PATENT DOCUMENTS

| | | | |
|---|---|---|---|
| 7,208,077 B1 | 4/2007 | Albers et al. | |
| 2002/0195345 A1 | 12/2002 | Bentsen et al. | |
| 2004/0023258 A1 | 2/2004 | Patolsky et al. | |
| 2004/0072158 A1* | 4/2004 | Henkens et al. | 435/6 |
| 2006/0006141 A1 | 1/2006 | Ufer et al. | |
| 2008/0099347 A1* | 5/2008 | Barlag et al. | 205/793.5 |
| 2008/0227086 A1* | 9/2008 | Vitzthum | 435/6 |

FOREIGN PATENT DOCUMENTS

| | | | |
|---|---|---|---|
| WO | 00/62048 | | 10/2000 |
| WO | 01/36958 | | 5/2001 |
| WO | 02/20838 | | 3/2002 |
| WO | 03/043945 | | 5/2003 |
| WO | WO03102541 | * | 12/2003 |
| WO | 2005/073705 | | 8/2005 |
| WO | 2005/073708 | | 8/2005 |
| WO | WO/2005/073708 | * | 8/2005 |

OTHER PUBLICATIONS

D. S. Bindra et al. "Pulsed Amperometric Detection of Glucose in Biological Fluids at a Surface-Modified Gold Electrode" Analytical Chemistry, vol. 61, No. 22, Nov. 15, 1989; pp. 2566-2570.

R. Thewes et al. "Sensor Arrays for Fully-Electronic DNA Detection on CMOS" IEEE, ISSCC 2002, No. 21.2; 3 pages.

R. Thewes et al. "CMOS-Sensoren für Life-Sciences" VDE-Kongress, Berlin 2004; pp. 81-88.

Office Action issued Aug. 7, 2008 in corresponding German Patent Application No. 10 2005 037 436.0.

International Search Report issued May 4, 2007 in corresponding International Patent Application No. PCT/EP2006/064842.

Office Action issued Nov. 14, 2008 in corresponding European Patent Application No. 06 778 077.5.

* cited by examiner

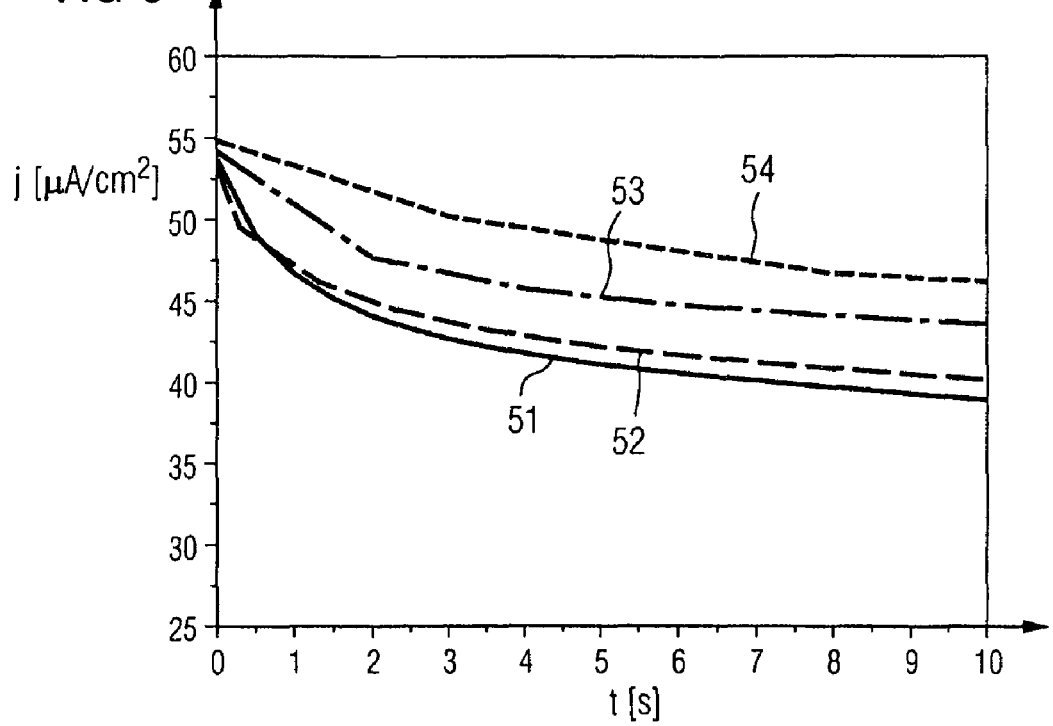
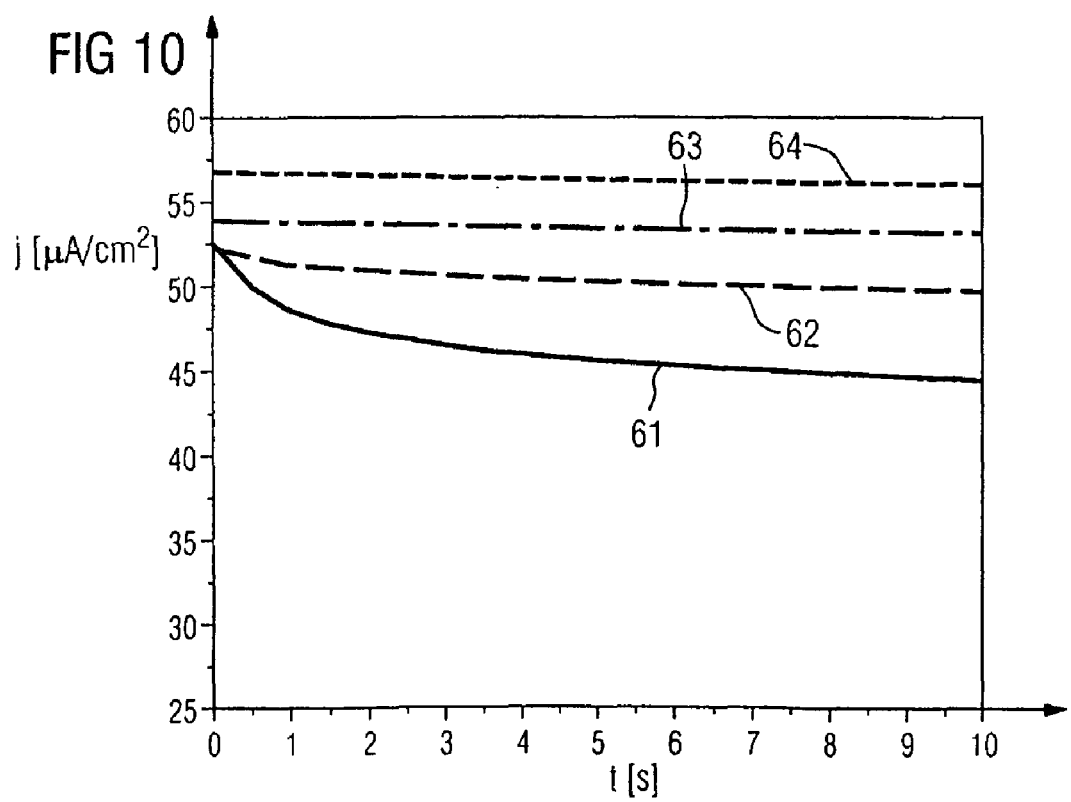

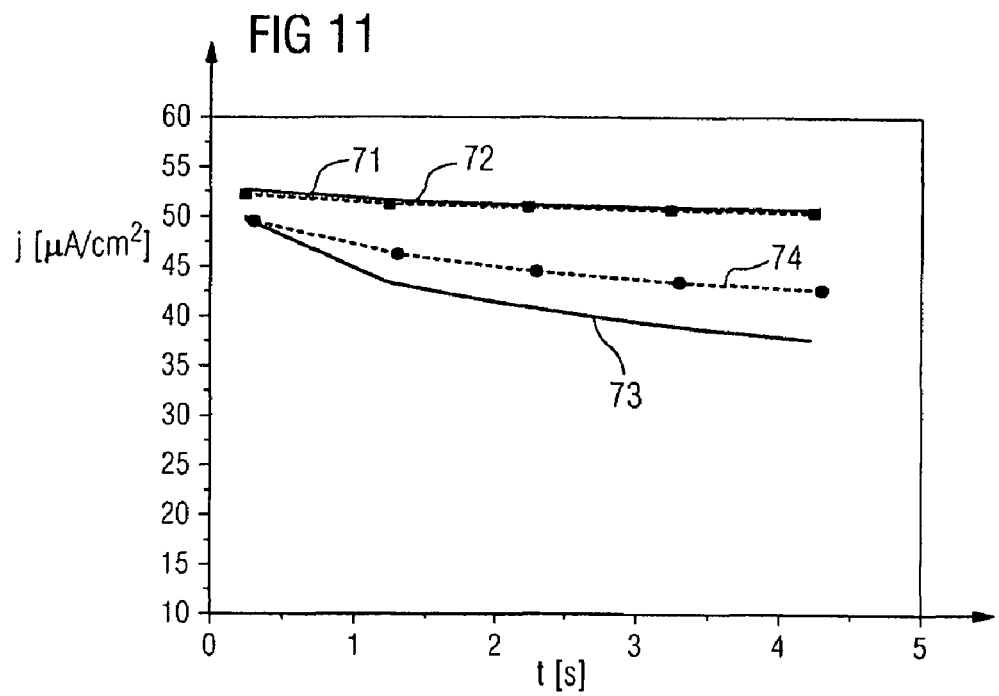
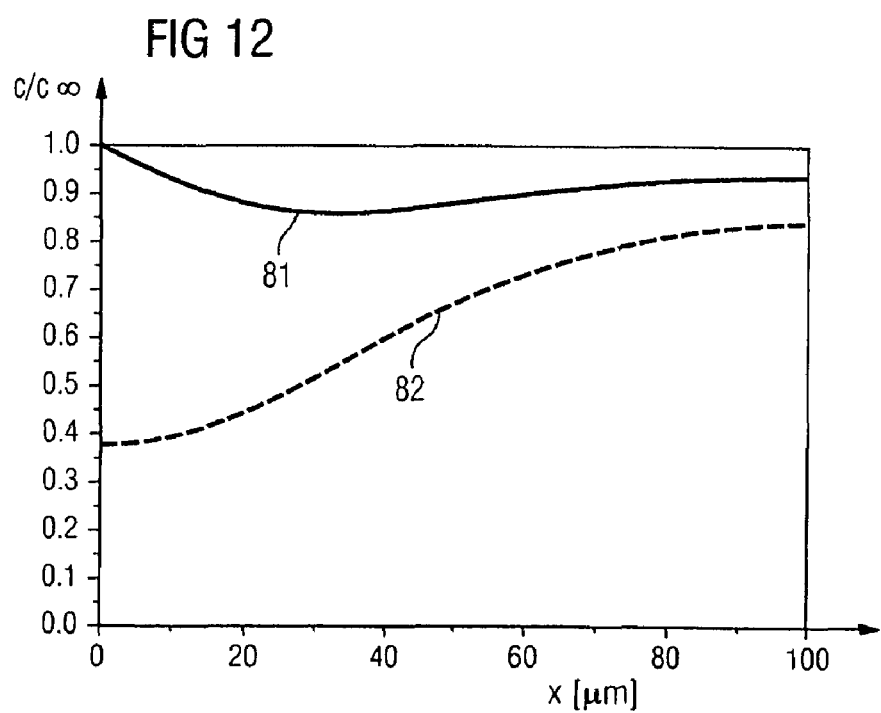

$111_i$

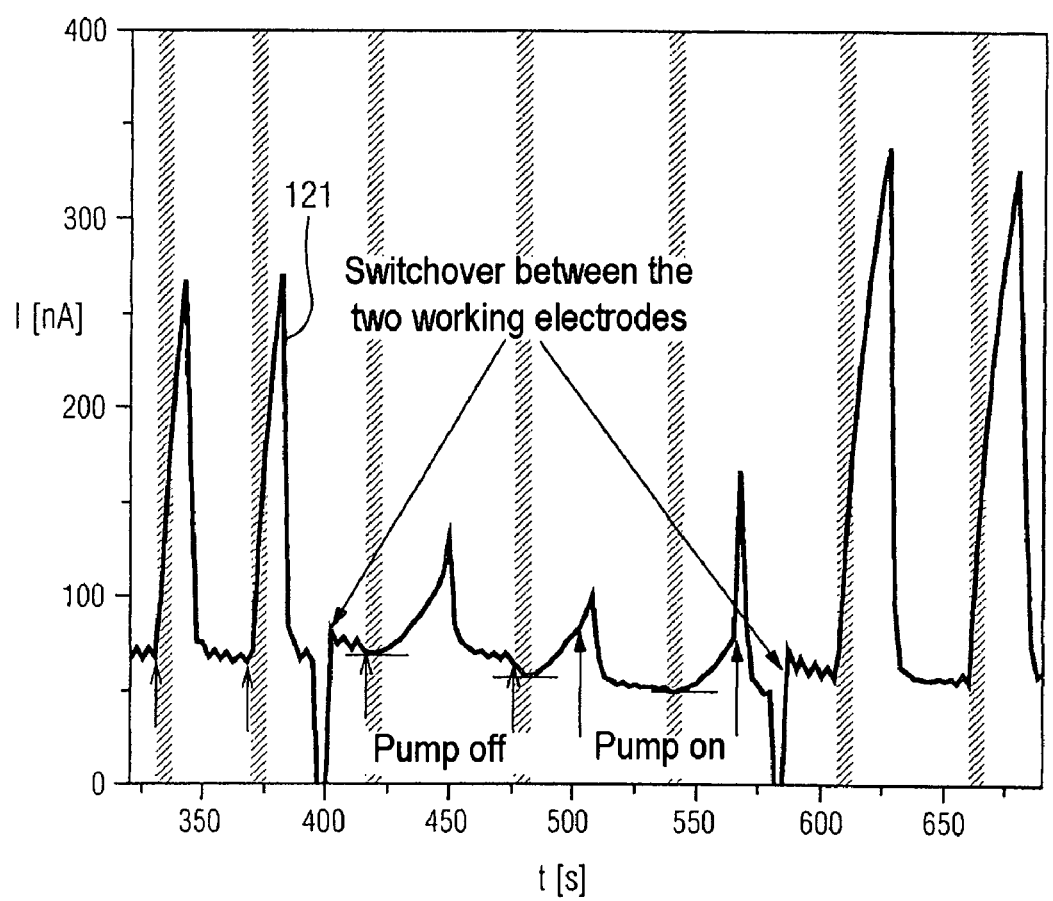

METHOD AND SYSTEM FOR DETERMINING THE CONCENTRATION OF AN ANALYTE/ENZYME COMPLEX OR OF AN ANALYTE/ENZYME CONJUGATE, ESPECIALLY FOR THE ELECTROCHEMICAL DETECTION OF THE ANALYTE, AND CORRESPONDING MEASURING DEVICE

CROSS REFERENCE TO RELATED APPLICATIONS

This application is based on and hereby claims priority to German Application No. 10 2005 037 436 0 filed on Aug. 4, 2005, and PCT/EP2006/064842, filed on Jul. 31, 2006, the contents of which are hereby incorporated by reference.

BACKGROUND

So-called biosensors are used for the determination of antibodies, antigens or DNA in blood, water, air or food. They are based on specific binding of the analyte to a capture molecule, for example of an antibody to an antigen or of a DNA sequence to the complementary DNA capture sequence. This binding event is often detected by optical methods. Fluorescent dyes are in this case introduced into the analyte, for example by PCR in the case of DNA analysis, and subsequently read out at the positions with different capture sequences. Such optical systems, however, are expensive and elaborate to handle. The required apparatus are sensitive and not suitable for field tests.

Electrochemical biosensors are a suitable alternative in this case.

Here, detection is carried out by the conversion of an electrochemical substance. Electrochemical detection is widespread, for example, in glucose sensors. The glucose is oxidized by a redox enzyme, namely glucose oxidase, and oxygen which is present is simultaneously reduced. The resulting hydrogen peroxide is then electrochemically oxidized again, and the glucose concentration is thus determined amperometrically. In refinements of these glucose sensors, mediators replace the oxygen. During the oxidation of glucose by the redox enzyme, the mediator, for example 1,1-dimethyl ferrocene, is simultaneously reduced. The electrochemical oxidation of the enzymatically reduced mediator, for amperometric determination of the glucose concentration, can take place at much lower potentials in this case, so that the measurement is more accurate and less susceptible to interference. In this context, many pulsed amperometric methods have been developed which determine not the total amount of redox mediator, but only that fraction which was previously reduced enzymatically.

For the electrochemical detection of binding events, however, the absolute quantity of a redox-active substance must be measured as sensitively as possible. The actual marker for the presence of the analyte at a sensor position is the enzyme per se. For DNA analysis, for example, a biotin marker is attached to the analyte during PCR. Various DNA capture sequences are bound to the different sensor positions on a biosensor. The analyte hybridizes only with the matching sequences, and the unbound analyte is washed away. A streptavidin-enzyme, for example alkaline phosphatase, is then bound to the biotin marker molecule in order to detect this binding event. If enzyme substrate is added, for example p-aminophenyl phosphate, then p-aminophenol is released by hydrolytic cleavage of the phosphate only at the sensor positions to which the analyte has bound.

The use of p-aminophenyl phosphate as a substrate for alkaline phosphatase is introduced in CLIN. CHEM 36/11, pp. 1941-1944 (1990), where a bead-based immunoassay is described. Here, alkaline phosphatase reveals whether analyte has bound to the bead-immobilized antibodies. The beads are incubated with p-aminophenyl phosphate and then the supernatant solution is examined for p-aminophenyl phosphate in a flow-injection analysis system. This solution flows through an electrochemical sensor, the working electrode of which is constantly polarized at about +0.1 V vs. Ag/AgCl reference electrode. Measurement in the flowing electrolyte or sample volume has the advantage that no significant depletion of the p-aminophenol takes place in front of the electrode. It is continuously replenished by the flow. Such a system, however, is not microsystem-compatible. The electrochemical sensor can read only one sample at a time, and the volumes required are large.

If an array of sensors with different capturers—whether DNA capture sequences or antibodies—is intended to be used, then the electrochemical detection must be carried out in a stationary electrolyte so that the sensors only detect the signal of the capturers immobilized directly thereon. The presence of the enzyme is revealed by a rise in the p-aminophenol concentration. Simple electrochemical sensors, in which the working electrode is at a constant potential, are not suitable for this. Owing to the conversion of the enzyme product taking place continuously, it will be consumed. A decrease in the concentration due to the measurement per se will thus be superimposed on the rise in the concentration due to the enzyme activity.

In order to circumvent this problem, U.S. Pat. No. 6,682,648 B1 proposes the use of interdigital electrode arrays. Each sensor consists of two interdigital electrodes. By a bipotentiostat, one of the electrodes is polarized positively and the other negatively. The p-aminophenol is oxidized at the first electrode and therefore consumed. If it can now diffuse to the second electrode, then it will be reduced again there and is once more available for the measurement at the first electrode.

A prerequisite for the latter redox cycling system is that the distance between the two electrodes should be very small, however, so that the transport of p-aminophenol and the oxidation product quinone imine by diffusion between the electrodes takes place rapidly enough, in respect of which reference may be made to the publication K. Aoki, J. Electroanal. Chem. 270 (1989), p. 35. In the aforementioned U.S. Pat. No. 6,682,648 B1, the use of interdigital electrodes with structure dimensions smaller than 1 µm is proposed for this purpose. The result of this is that the production of a biosensor array with such interdigital electrodes is elaborate and expensive.

Further information about the measurement, especially in liquids, or for biochemical measurements is given in DE 43 35 241 A1, DE 41 31 731 A1, DE 197 17 809 U1 and DE 199 17 052 A1. A method for the electrochemical measurement of redox cycling with a practicable electrode arrangement is described in detail in WO 01/67587 A1.

SUMMARY

Based on references above, it is one potential object to provide a method and a system with which it is possible to determine concentrations of a redox-active substance in 1 µM concentrations on arrays of flat electrodes with diameters $\geq$30 µm, preferably $\geq$50 µm. The system is not intended to be convective, i.e. neither an electrode nor the solution is stirred or moved, and the measurement frequency is intended to be $\geq$0.5 Hz. It is also an object to provide an associated measuring device.

The inventors propose that the potential of the working electrode should be pulsed, which has already been proposed in a different context. Furthermore only alternating measurement phases and relaxation phases are moreover set up the measurement phase pulse lengths being selected so that the capacitive current toward the end of the measurement phase is small compared with the Faraday current, and the relaxation phase pulse lengths being selected so that the concentration gradient is relaxed toward the end of the pulse, such that the concentration change of the redox-active enzyme product—due to consumption of the enzyme product by the measurement per se—is substantially reversed at the start of the following measurement phase. The current measured at the end of the measurement phase therefore constitutes a significant measurement signal, which is not to be expected "a priori".

According to the inventors, the rapid measurement of the concentration and in particular the concentration change of an enzyme product in molecular-biological detection systems is carried out by the electrochemical redox reaction of the enzymatically formed redox-active substance on the working electrodes anchored in caverns on a chip band by cyclic pulse application, the current measured after the decay of the charge redistribution in the double layer forming the measurement signal.

A potential basis of the proposed method and device is the discovery that, with a suitable measurement method for determining the concentration of a redox-active substance, measurement can advantageously be carried out on electrodes with diameters of the order of a few 100 μm up to 1 cm. In particular, complexly constructed interdigital electrodes are no longer necessary. Now, in particular, it is even possible to use economical transducer arrays such as those described in detail for example in German Patent Application AZ. 10 2004 004 654.9-52 having a common assignee with the present application (not published at the priority date of this application).

The measuring structure in the associated measuring device simplified compared with redox cycling, is to such an extent that a bipotentiostat is not required. A simple potentiostat in combination with a pulse generator is sufficient.

A steady state is not set up—as it is in known redox cycling, rather a rapid relaxation of the concentration gradient is induced electrochemically. To this end, the potential of the working electrode is pulsed. A diffusion layer is formed whose thickness reaches a maximum value, which depends on the length of the measurement phase, at the end of the measurement period. For measurement of oxidation currents, a sufficient reduction potential is set up during the relaxation phase. The species oxidized during the measurement phase and still present in front of the electrode are reduced again, and the concentration gradient and therefore the diffusion layer are therefore removed.

Thus, instead of establishing constant diffusion layer thicknesses as in redox cycling, the diffusion layer is temporarily built up and removed again in the "forced relaxation amperometry". In both cases, a diffusion layer thickness limited at least in its maximum value is set up. If the intention is to observe reduction, then the reduction potential must be set up during the measurement phase and a corresponding oxidation, potential must be set up during the relaxation phase.

BRIEF DESCRIPTION OF THE DRAWINGS

These and other aspects and advantages will become more apparent and more readily appreciated from the following description of the exemplary embodiments, taken in conjunction with the accompanying drawings of which:

FIG. 9 shows a graphical representation of the dependency of the current density on time, FIG. 10 shows a representation corresponding to FIG. 5 for the relaxation phase, FIG. 11 shows a representation corresponding to FIG. 5 with comparison of experimental and calculated values, FIG. 12 shows a graphical representation of the dependency of the concentration on the electrode spacing, FIG. 17 shows the profile of a typical measurement with a measurement current curve.

DETAILED DESCRIPTION OF THE PREFERRED EMBODIMENT

Figure 1:
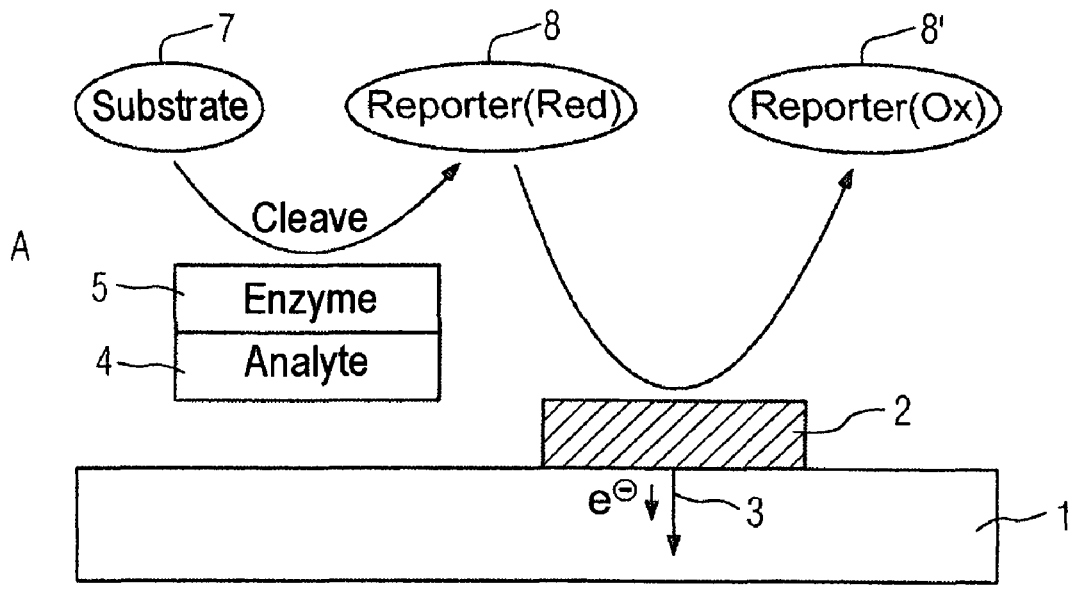
FIG. 1 to FIG. 4 schematically show the methodology in order to illustrate the proposed method and device.
Figure 2:
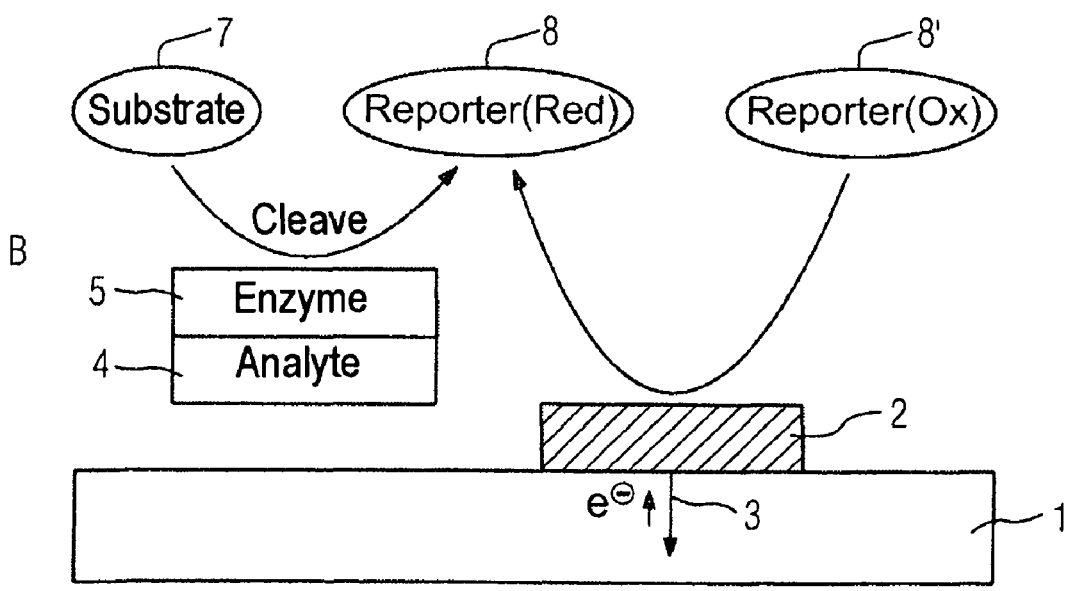

Reference will now be made in detail to the preferred embodiments, examples of which are illustrated in the accompanying drawings, wherein like reference numerals refer to like elements throughout.

The methodology of so-called "Forced Relaxation Amperometry (FRA)" will initially be described in FIGS. 1 to 4. It will be assumed that the methodology of redox cycling is known per se from the related art.

Figure 3:
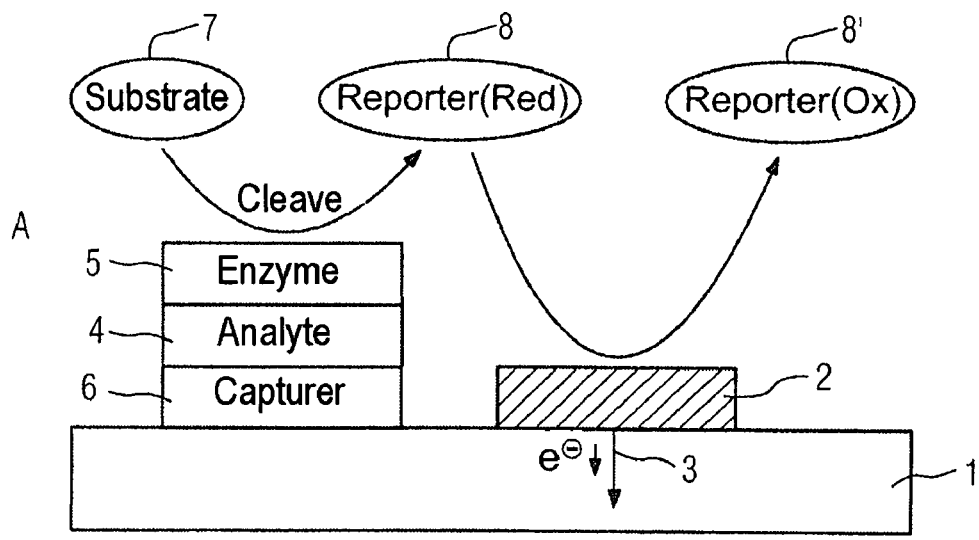
Figure 4:
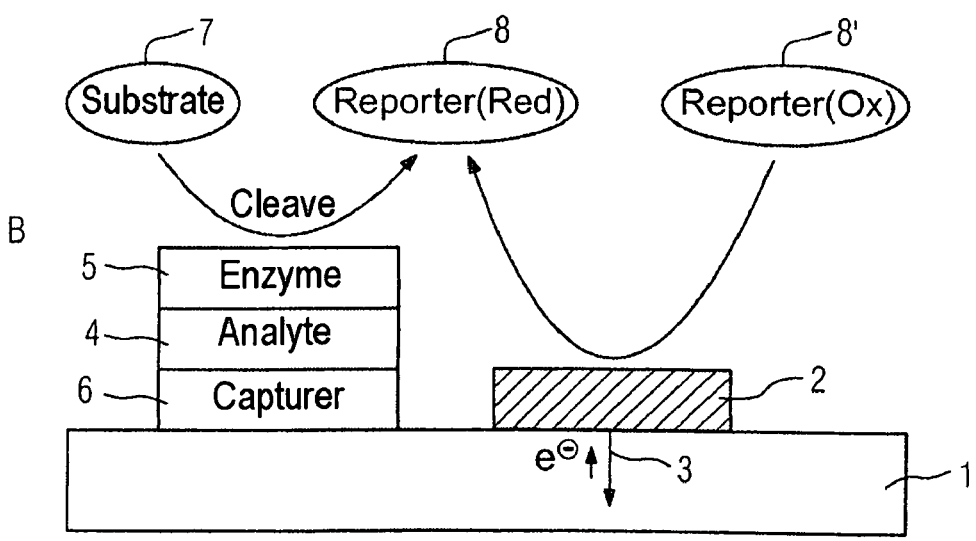
Figure 5:
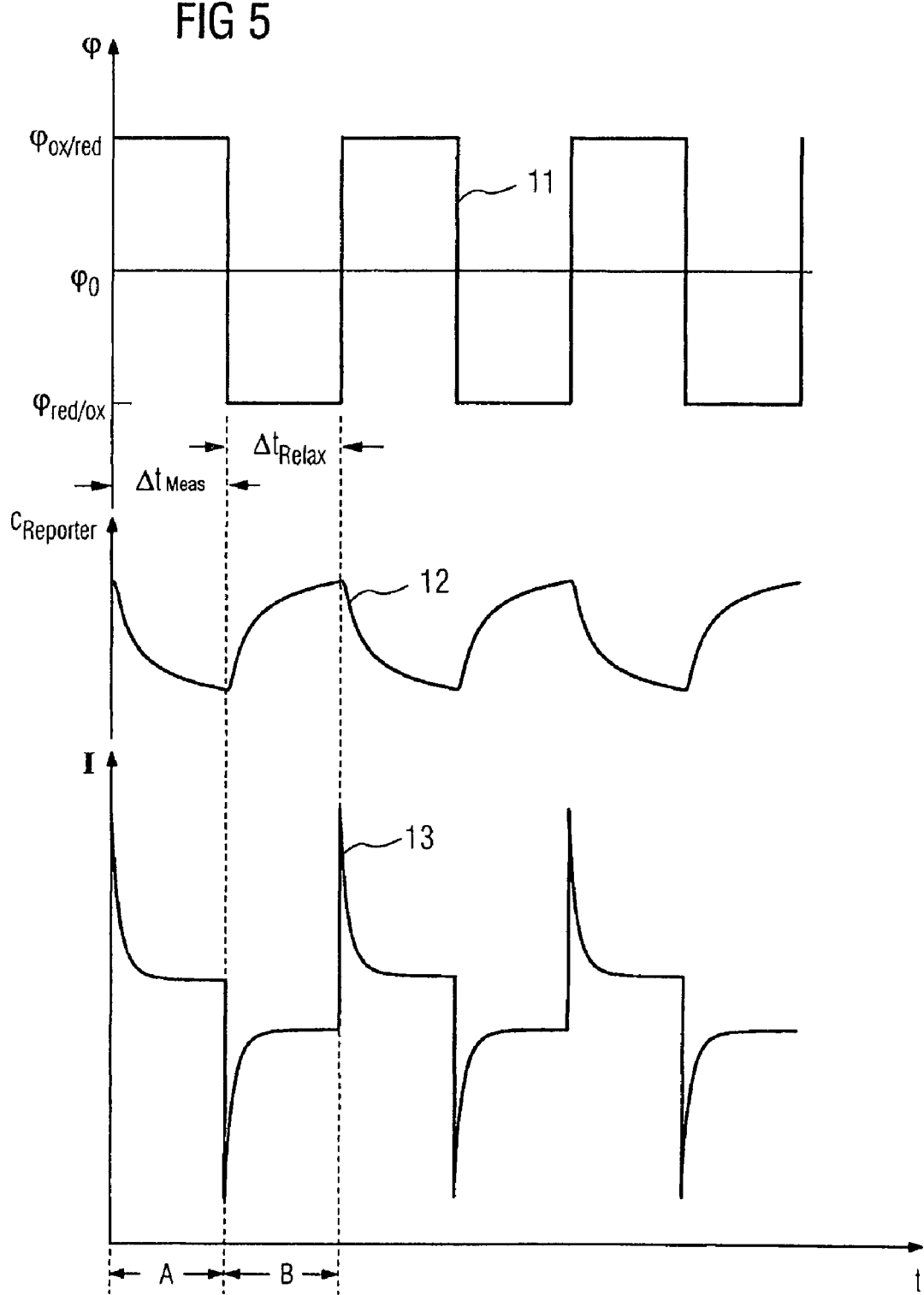
FIG. 5 shows a graphical representation of forced relaxation amperometry with response curves for pulse lengths and associated concentration and signal curves.

FIG. 5 represents the associated signal curves for the FRA method defined with the aid of FIGS. 1 to 4. Illustrations of the accuracy of the new measurement method are subsequently given with the aid of FIGS. 6 to 12, and a specific measuring device is finally depicted in FIG. 13. This indicates an exemplary transducer array, the structure of which is shown in FIGS. 14 and 15. FIG. 16 shows a different transducer array. Lastly, FIG. 17 illustrates the conduct of the method when using the arrangement as a DNA sensor.

In detail, reference 1 in FIGS. 1 to 4 denotes a support for at least one measurement electrode 2 to which a current path 3 for an electron flow is assigned, an analyte 4 being provided. The electrode 2 may be formed from a noble metal. An enzyme 5 is also present, the concentration of which represents a measure of the concentration of the analyte 4 by its being bound directly or indirectly to the analyte 4 or being displaced by the analyte 4.

For binding to the support 1, a capturer 6 is indicated in FIGS. 3 and 4. Reference 7 identifies a substrate which is converted by the enzyme 5 by hydrolytic cleavage, leading to the formation of a reporter molecule 8 which can be electrochemically converted reversibly under conditions in which the substrate 7 is stable.

The arrangement comprising the support 1 and the electrode 2 constitutes a sensor. The electrode 2 is polarized for the duration of a measurement phase A so that the reporter molecule is oxidized or reduced, and it is polarized for the duration of a relaxation phase B so that the oxidized or reduced form of the reporter molecule 8 is respectively reduced or oxidized again at the same electrode 2. This is illustrated by FIGS. 3 and 4. The current flowing during the measurement phase A is therefore a measure of the concentration of the substrate 7 converted by the enzyme 5.

It is advantageous for the analyte to contain a marking element, and for the enzyme to contain a coupling element which binds specifically to the marking element of the analyte. The enzyme may also be bound directly to the analyte. In the known way, a capture molecule which binds specifically to the analyte is in this case immobilized on or in the vicinity of an electrode.

Further embodiments are obtained by the introduction of an auxiliary molecule, which is a molecule that contains a marking element and binds specifically to the capture molecule. If this auxiliary molecule is bound to the enzyme directly or via a coupling element, then displacement of the auxiliary molecule by the electrolyte will be revealed by a reduction in the amount of enzyme in front of the electrode. A decreasing measurement signal thus indicates specific binding of the analyte to the capture molecule.

Another embodiment employs an auxiliary molecule which binds specifically to the analyte and is likewise bound to the enzyme directly or via a coupling element. The analyte binds to the capture molecule and the auxiliary molecule in turn binds to the analyte. The capturer-analyte-auxiliary molecule-enzyme binding complex is revealed by an increasing measurement signal. A particular advantage here is that the analyte does not need to contain a marking element.

The various phases during the measurement are indicated in FIG. 5. Which is the measurement phase and which is the relaxation phase depends on whether an oxidation or reduction current is intended to be measured. The pulse lengths for oxidation and reduction need not be equal, i.e. the times $t_{ox}$ and $t_{red}$ may differ. Furthermore, the potentials $\phi_{ox}$ and $\phi_{red}$ need not be symmetrical with the redox potential $\phi_0$ of the species.

The representing in FIG. 5 shows the possible potential profile when using square-wave pulses. The potentials $\phi_{ox}$ or $\phi_{red}$ and the times $t_{ox}$ and $t_{red}$ are plotted with the pulse waveform 11 in arbitrary units. The pulse waveform 11 need not be symmetrical with the pulse lengths for oxidation and reduction. It is likewise possible to carry out forced relaxation amperometry with sawtooth voltage curves or sine curves.

Specifically, the measurement phase is denoted by A and the relaxation phase by B in FIG. 5. Besides the potential curve 11, a curve 12 is furthermore represented for the concentration of the enzyme product in front of the electrode together with the electrical current 13 as a measurement signal. The current value crucial for the process is thus respectively obtained at the end of the relaxation interval, and is a measure of the relaxed concentration change.

For further consideration, it will be assumed that the concentration of a molecule present in its reduced form is intended to be measured. In this case, the potential during the measurement phase is positive relative to the redox potential of the species. The highest measurement currents are reached when the potential is so positive that a diffusion limit current is set up. The current is then limited not by the kinetics of the redox reaction, but only by the diffusion.

The development of the concentration profile of the reduced species as a function of time is given by the corresponding solution of Fick's law for diffusion into the singly infinite half-space, i.e.:

$$c(t, x) = c_\infty \cdot \mathrm{erf}\left(\frac{x}{2\sqrt{Dt}}\right), \; s \to \infty \qquad (1)$$

where:

c: concentration as a function of time and position
$c_\infty$: concentration in the solution ($x \to \infty$)
erf: error function
D: diffusion coefficient
s: extent of the electrolyte space in front of the electrode A further increase in the measurement signal may be achieved by limiting the electrolyte space in front of the electrode. The reporter molecule formed by the enzyme diffuses only partly to the electrode. The other part diffuses into the electrolyte space away from the electrode. If the electrolyte space is now reduced until it is smaller than the diffusion length during the measurement phase, then saturation of the electrolyte space with reporter molecule will occur during the measurement phase and any further reporter molecule that is formed will increase the concentration in front of the electrode. This applies for the total concentration of reduced and oxidized reporter molecule. But since a very small electrolyte space makes it difficult to carry out the biochemical assay, this entails the requirement for an electrolyte space with variable height. Only at the start of the measurement is the electrolyte space reduced and the sensitivity of the sensor therefore increased.

Figure 6:
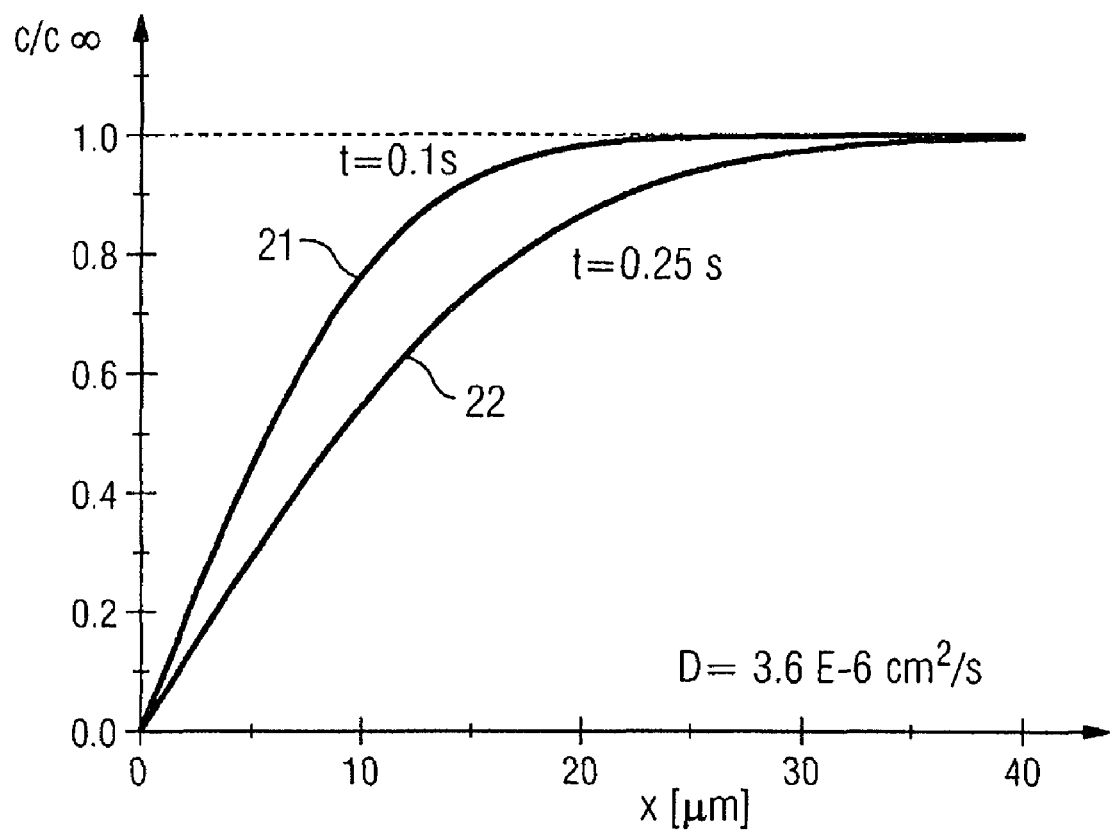
FIG. 6 shows a graphical representation of the dependency of the relative concentration on the spacing of the electrodes.

Reducing the electrolyte space furthermore decreases the amount of reporter molecule which travels by diffusion from the electrolyte space above one sensor to the electrolyte space above a second sensor. Vitiation of the sensor signals due to neighboring sensors is thereby reduced, and the selectivity of the sensor array is improved. FIG. 6 shows two concentration profiles 21 and 22 for a substance having a diffusion coefficient D=3.6E−6 cm$^2$/s. This corresponds to the diffusion coefficient of para-aminophenol (pAP) which will be used as an example below to demonstrate the functionality of "forced relaxation amperometry", the chemical reaction for which is given below:

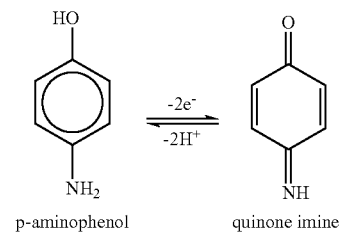

p-aminophenol      quinone imine

After 0.1 s, the diffusion layer has a thickness of about 25 μm. After 0.25 s, the extent of the pAP-depleted layer is already 40 μm. The thicker this layer is, the longer the relaxation by diffusion takes.

Figure 7:
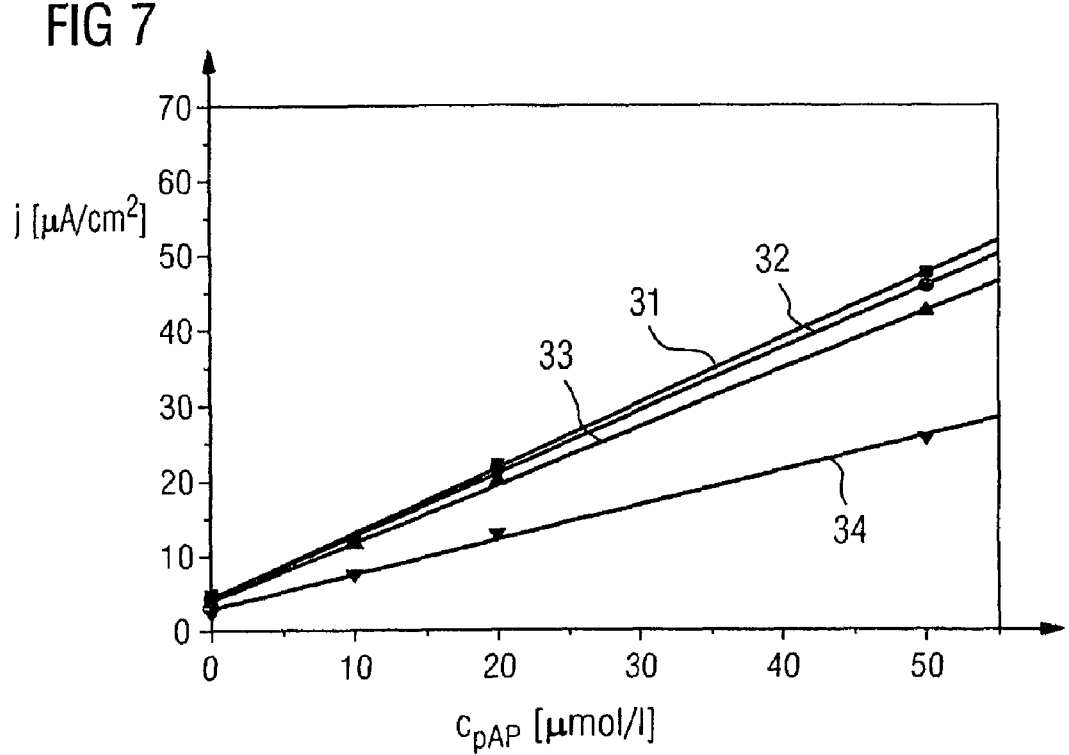
FIG. 7 shows a graphical representation of the current on the concentration and FIG. 8 shows a graphical representation of the gradient as a function of the potential during the relaxation phase.
Figure 8:
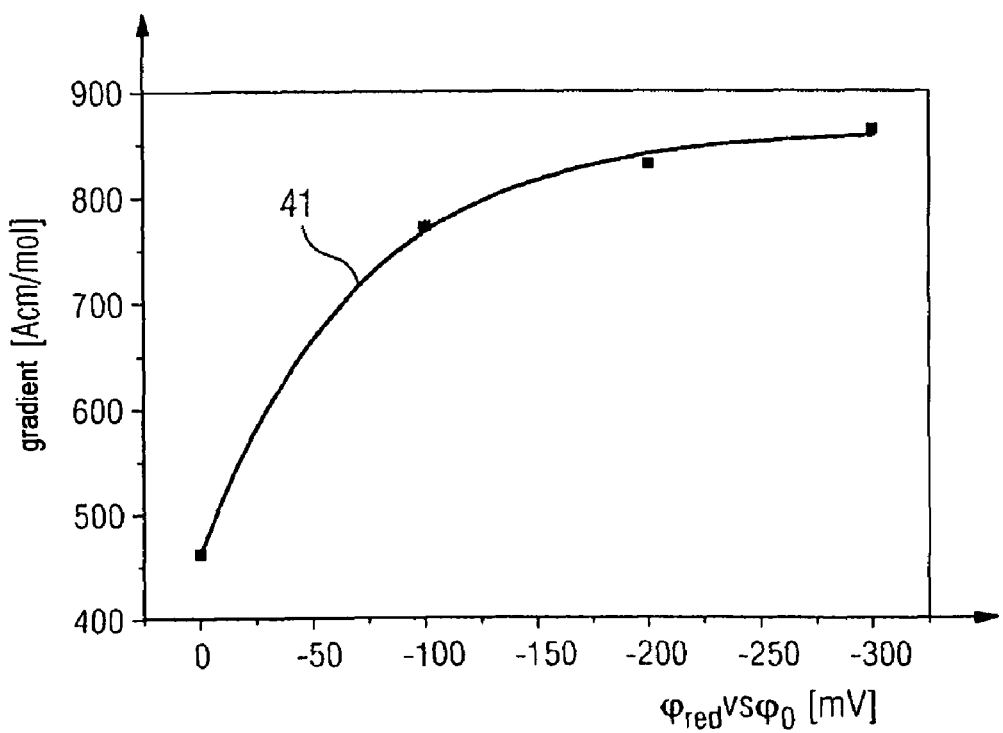

FIG. 7 shows the current density as a function of the pAP concentration in the solution for various pulse sequences, which are denoted by response curves 31 to 34. The measurement phase always lasts 0.25 s, and the relaxation phase 0.75 s. The current is measured 0.24 s after the start of the measurement phase. The oxidation current during the measurement phase is +200 mV relative to the redox potential. The potential during the relaxation phase was varied. It assumed values of between −300 mV and 0 mV relative to the redox potential. Specifically:

| 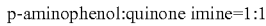 | for response curve 31 | −300 mV/200 mV, |
|---|---|---|
| | for response curve 32 | −200 mV/200 mV, |
| | for response curve 33 | −100 mV/200 mV, |
| And | for response curve 34 | 0 mV/200 mV. |

With these parameters, different gradients of the current density j are obtained in respect of their functional dependency on the pAP concentration.

The gradient of the current density with the pAP concentration, i.e. the sensitivity of the measurement, increases constantly as the potential during the relaxation phase becomes more negative. Plotting the gradient against the relaxation potential according to FIG. 4 clearly shows the advantageous effect of forced relaxation amperometry by the response curve 41.

While the gradient is only 462 Acm/mol with a relaxation potential of 0 V vs. $\phi_0$, this value increases to 864 Acm/mol with −300 mV vs. $\phi_0$. This doubling is based on the improved redox cycling effect, while with a relaxation potential of −300 mV vs. $\phi_0$ the quinone imine in front of the electrode is fully reduced to p-aminophenol (pAP). With a relaxation potential of 0 V vs. $\phi_0$, however, according to Nernst's equation a concentration ratio p-aminophenol:quinone imine=1:1 is set up directly in front of the electrode. The quinone imine is thus only partially reduced again.

The increase in sensitivity is only one advantage of "forced relaxation amperometry", but it is a crucial one. The constancy of the current signal even during the first seconds of the measurement is another essential advantage.

In order to determine the sensitivity, the current density set up after a prolonged measurement time was used. For measuring the enzyme activities, for example, the measurement is however carried out with the solution initially being stirred or pumped. The pAP formed by the enzyme is thereby flushed away and a constant basic current is set up. The pump is then stopped and the concentration rising during the first seconds is measured. Typical gradients are of the order of 2 μA/cm²s. If the measurement per se now leads to a reduction in the signal, then the two effects are superimposed and an insufficient gradient of the current and therefore enzyme activity is measured. Since this reduction of the current due to consumption of the substance furthermore depends on its concentration, this effect cannot be eliminated by normalizations.

Experiments with a constant concentration provide information about the temporal signal constancy. The concentration was 50 μM pAP, and the potential during the measurement phase was +200 mV. The duration of the measurement phase was 250 ms, the current being measured after 240 ms. The potential during the relaxation phase was 0 V vs. $\phi_0$ in a first experiment, and −300 mV vs. $\phi_0$ in a second experiment. The duration of the relaxation phase was varied between 250 ms and 4.75 s.

The time dependency of the current density j is shown in a graphical representation in FIG. 9: in response curves 51 to 54 are obtained for different relaxation phase durations $\Delta t_{red}$, specifically between 0.255 and 4.755. The currents decrease significantly during the first 10 s of the measurement. With a relaxation phase length of 0.25 s, the decrease was 14 μA/cm² in 10 s. When the duration of the relaxation phase is increased to 4.75 s, the decrease in the signal is reduced to 9 μA/cm² in 10 s. Thus, the shorter the duration of the relaxation phase is, the greater is this decrease in the signal with time. Yet even with long relaxation times, the decrease of 0.9 μA/cm² in 10 s is still considerable compared with the gradients of the order of 2 μA/cm²s which are intended to be measured in the application.

If the potential during the relaxation phase is now lowered to −300 mV, then the signal constancy is improved significantly. This is revealed in particular by FIG. 6, which shows a representation corresponding to FIG. 5 with response curves 61 to 64 for the same relaxation phase parameters $\Delta t_{red}$.

With a relaxation time of 0.25 s, the signal decrease is still 8 μA/cm² in 10 s. With a relaxation time of 0.75 s this value is still 2 μA/cm² in 10 s, with 1.75 still 1 μA/cm² in 10 s and for 4.75 s only 0.5 μA/cm² in 10 s. Even with a relaxation time of 0.5 s i.e. a measurement frequency of 1 Hz, and a relaxation potential of −300 mV, the signal decreases and therefore the error is only about 1% of the expected measurement value.

These experiments show the effect of the duration and potential of the relaxation phase on the measurement signal. Simulation calculations can provide further demonstration of the effect of forced relaxation amperometry. For this, on the one hand the current density during the redox cycling is calculated and, on the other hand, the current density without redox cycling is determined for comparison.

For the simulation with redox cycling, it was assumed that the electrolyte space has a thickness of 100 μm. Both the oxidation and the reduction potential are selected so that the reaction takes place in the diffusion limit current range, i.e. the currents are maximal. The pulse lengths are 250 ms for the oxidation potential and 750 ms for the reduction potential. The parameters for the calculations without redox cycling were the same, except for the fact that no potential is set during the relaxation phase and no current can flow through the potentiostat. At this time, the system is thus electrochemically decoupled.

The simulation data were compared with the experimental results for the corresponding pulse lengths and the potentials $\phi_{ox}$=+200 mV and $\phi_{red}$=−300 mV. These potential limits correspond most closely to the settings for the simulation. The y axis intercepts of the simulation data were fitted to the experimental results.

FIG. 11 shows a good match of experiment and simulation for forced relaxation amperometry, 71 representing the measured values and 72 the calculated response curves. At 2 μA/cm² in 4 s, the decrease in the current density under these conditions is small. Without "forced relaxation amperometry", however, the current density decrease during the first 4 s is already 12 μA/cm², which is illustrated by the response curve 73. The results for a measurement method with potentiostatting during the relaxation phase at the redox potential lie in between, which is illustrated by the response curve 74.

The improvement of the signal constancy by a factor of 6 may be attributed directly to the concentration profiles. The next figure shows the calculated concentration profiles of pAP as a function of the distance from the electrode, as are found at the end of the 5$^{th}$ relaxation phase.

In "forced relaxation amperometry", the previously formed oxidation product is reduced again during the relaxation phase. The concentration of pAP directly in front of the electrode has therefore risen again to the original value $c_\infty$ at the end of the relaxation phase. Further away from the electrode, the concentration is only slightly lowered. Without "forced relaxation amperometry", however, the concentration in front of the electrode is only 38% immediately before the next measurement phase. The concentration is also significantly reduced further away from the electrode.

The latter is also revealed in detail by FIG. 12 with response curves 81 and 82: the example according to response curve 82 for a measurement without redox cycling corresponds in practice to measuring the concentration of a substance which can indeed be oxidized, although its oxidation products cannot be reduced again. The situation would also be similar for a substance which can be reduced, but whose reduction products cannot be oxidized again. In the case of a biochemical sensor, this might for example be naphthol which like pAP can be released by an enzymatic reaction.

The measuring device is also shown in detail by FIG. 13: as well as by a transducer array 100 which will be described in detail with the aid of FIGS. 14 and 15, the measuring device is formed essentially by a suitable potentiostat 105 in combination with a pulse generator 106, which optionally delivers square-wave, sawtooth or sine pulses. Using two operational amplifiers 107 and 107' one of which is connected to "ground potential", and a defined measuring resistor 108, the potentiostat 105 is designed so that suitable potentials can be provided. The pulse length, the repetition rate and the height of the potential can be specified. In particular, the pulse lengths of the measurement phases and the relaxation phases can be adjusted separately, and may be of different length. The potentials may also be of different magnitude.

The transducer array 100 is assigned individual electrodes which, according to their purpose, form a reference electrode RE 104b, a counter electrode CE 104c and at least one measurement electrode WE 104a (=working electrode). These electrodes are connected as a three-electrode arrangement to the potentiostat 105. The signal of the potentiostat 105 is connected to a signal processing unit (not represented in detail in FIG. 9) by which evaluation is carried out while taking into account the above comments regarding measurement method and accuracy. The transducer array 100 includes metal regions $110_i$, sensor surface $111_i$, and opposite side $112_i$. In general, the signal waveform represented as $I_{out}$ in FIG. 13 is obtained for evaluation.

FIGS. 14/16 depict the transducer array 100, which is planar and flexible and in particular economical to produce, as part of the measuring device. What is essential here is that measurement by forced relaxation amperometry can now be carried out with a simplified transducer array 100. FIGS. 14 and 15 show the upper and lower sides of the transducer array 100, which has metal substrate 101 and an insulator layer 102. On the upper side, for example circular indentations $103_i$ are represented, which are referred to as cavities. The cavities $103_i$ are obtained by structuring the insulator 102. On the base of the indentations $103_i$, the upper side of the metal substrate is exposed and forms a measurement point when an analyte is applied.

The representation of the rear side shows by lines the structuring, and therefore separation of the metal substrate 101 into mutually isolated parts. Each metal island corresponds to an indentation $103_i$ on the front side. Possible contact sites for a so-called needle card, for simplified electrical contacting of the metal surfaces, are indicated by dots. What is essential here is that a plurality of metal islands, preferably three, with an analyte define a sensor and are suitable for carrying out electrochemical measurements with the associated electrodes which comprise a measurement electrode WE, a counter electrode CE and a reference electrode RE.

In another configuration, however, transducer arrays in CMOS technology may also be used, which will be described with the aid of FIG. 16:

In FIG. 16, a multiplicity of microcavities 200 for carrying out a biochemical analyses are arranged on the sensitive surface of the sensor or support 1. There are m×n elements 201 arranged in rows and columns as a transducer array 200. What is essential here is that biochemical reactions or measurements can take place simultaneously in the individual cavities, without the possibility of crosstalk of the reactions from a first cavity into a second cavity taking place when substances are added.

In FIG. 16, discrete electrical contacts are applied on the support 1 with the sensitive surface, or the individual sensitive elements. The contacts form inputs for the electrical measurement circuit. For example, there are two supply voltage inputs $V_{dd}$, $V_{ss}$, an input GND for ground potential, an input for a clock signal, an input for a control voltage and an input for a reset signal. A multiplexer 210, a "Gray counter & decoder" 215 and an amplifier 220 are furthermore integrated on the chip 1 by standard silicon technology. The measurement signal is acquired at the output 'out'; in the case of an array arrangement with a multiplicity of cavities as m×n individual sensors, a multiplex signal is obtained which is read out for example with a frequency of 10 kHz.

The multiplex signal output on a single line 'out' is a pattern of discrete voltage values, from which the individual sensor signals are obtained by a demultiplexer in an evaluation apparatus.

Figure 13:
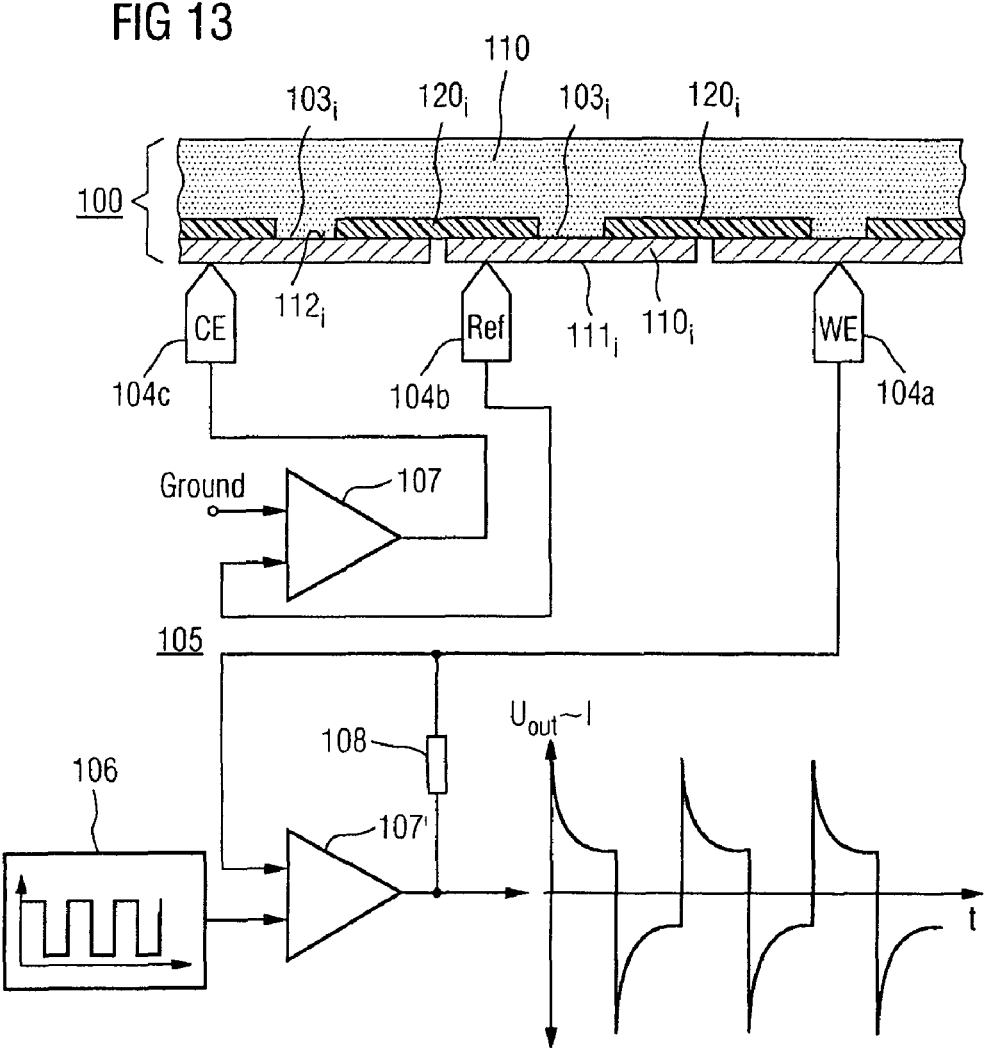
FIG. 13 shows a measuring device for forced relaxation amperometry with an associated transducer array, FIGS. 14/15 show a first transducer array for the measuring device according to FIG. 1 as seen from above and below.
Figure 14:
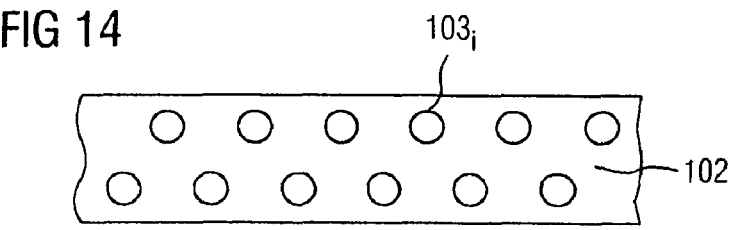
Figure 15:
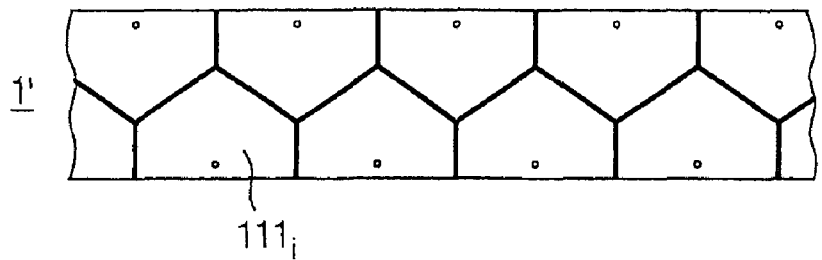
Figure 16:
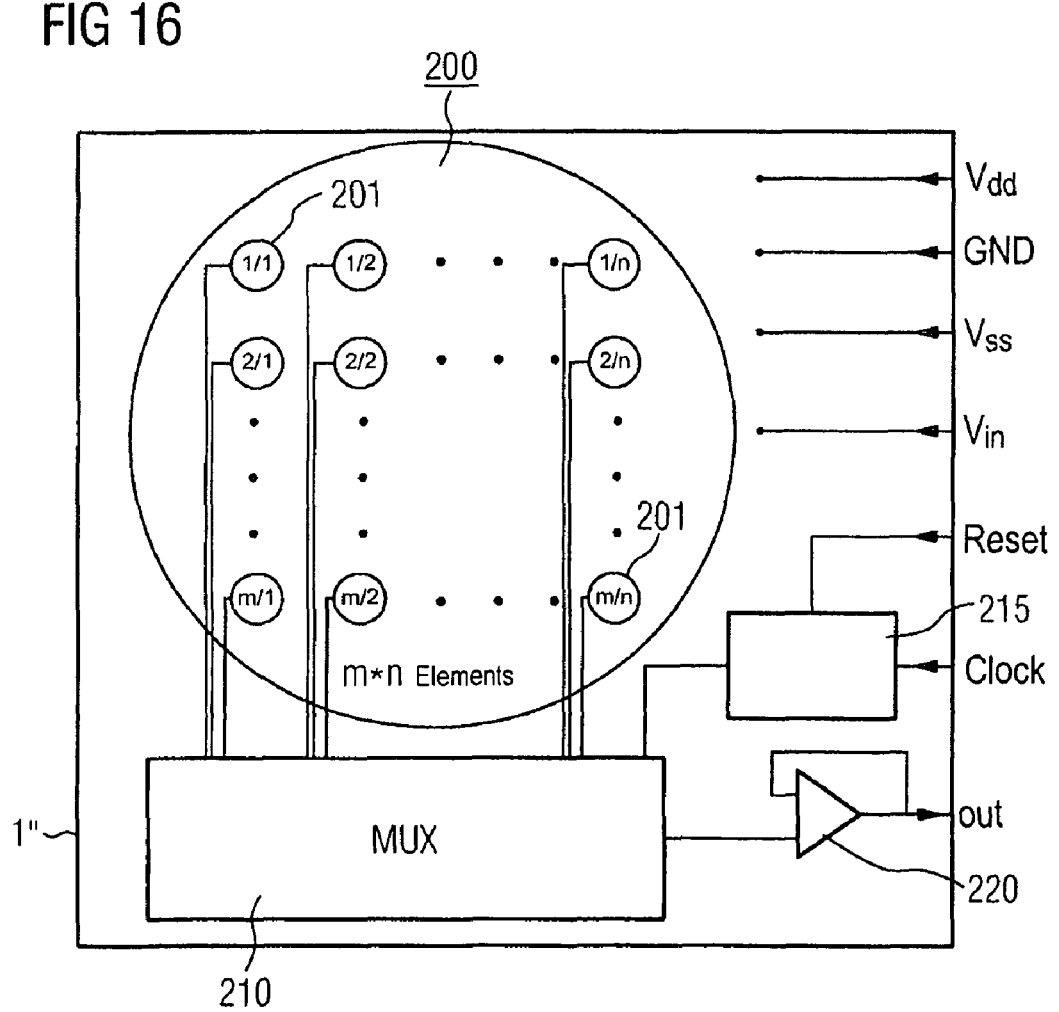
FIG. 16 shows a second, silicon-based transducer array in plan view.

A transducer array in thin-film technology on a rigid substrate is thus used in an alternative measuring arrangement in FIG. 16, instead of the self-supporting and flexible transducer array according to FIGS. 13 to 15. Flat electrodes are provided in this case, which have an extent that is greater than the diffusion length. A typical diffusion length for the example indicated above is 25 µm, so that the flat electrodes have an extent $\geqq 30$ µm, preferably $\geqq 50$ µm.

The rigid substrate is in particular silicon, which is preferably provided with an insulator layer.

The proposed redox cycling may also be carried out with such transducers as are compatible with CMOS technology for the signal processing.

With an arrangement according to FIG. 13 and a transducer array 100 or 200, alternatively according to FIGS. 14/15 or according to FIG. 16, a biochemical sensor for DNA analysis is produced by way of example: for example, the transducer array 100 described with the aid of FIGS. 14/15 is used, comprising a metal layer and an insulating layer with cavities $3_i$ connected thereto. The diameter of the cavities $3_i$ is 0.8 mm, the depth 90 µm and the distance between two neighboring measurement points 1 mm. The electrode surfaces are covered with a 2.3 µm thick gold layer.

In the device thus described, the height of the electrolyte space above the transducer array can be varied during the assay. The electrolyte space above the transducer array may be bounded by a flexible material, in which case the flexible material may be pressed in the direction of the array by a force acting from above. The electrolyte space is therefore reduced to such an extent as to prevent transporter molecules from being transported between the sensors of the array.

Overall, the sensor arrangement for the above application thus includes at least three, but preferably four electrodes. One of the electrodes is then covered with a silver/silver chloride (Ag/AgCl) layer as a reference electrode, another electrode is used as the counter electrode CE and the two other electrodes are used as measurement electrodes WE.

On one of the measurement electrodes, a synthetic oligonucleotide sequence with a length of 25 is anchored by a terminal thiol group on the gold surface as a positive sample. The second measurement electrode remains free as a negative sample. The two surfaces were then incubated for 15 minutes with a solution of 1 mg bovine serum albumin per ml, and the sensor array was subsequently put into a 100 µm deep flow channel. First, 10 µl of a 10 µM biotinylated target sequence are pumped over the electrodes within about 5 minutes. Then, after a washing step, a solution of streptavidin-labeled alkaline phosphatase is added thereon. The washing is carried out with a buffer solution of 100 mM tris(hydroxymethyl)aminomethane titrated to pH 8 with hydrochloric acid and 130 mM NaCl. After the washing again, a 2 mM solution of the enzyme substrate para-aminophenol phosphate (pAPP) in the buffer solution is pumped over the sensor array. In the presence of the enzyme alkaline phosphatase, the enzyme substrate pAPP is converted to para-aminophenol (pAP).

For the measurement, the reference electrode RE, the counter electrode CE and one of the two measurement electrodes WE are respectively connected in a three-electrode arrangement to the potentiostat. The measurement is carried out by "forced relaxation amperometry". During the measurement phase, the para-aminophenol formed by the enzyme is oxidized to quinone imine. The oxidation potential $\phi_{ox}$ is +200 mV vs. $\phi_0$. In the relaxation phase, the quinone imine that has been formed is reduced again to para-aminophenol, specifically with $\phi_{red}=-200$ mV. The pulse length of the measurement phase is 250 ms, and that of the relaxation phase 750 ms. The current is measured 240 ms after the start of the measurement phase.

The positive sample, i.e. the electrode with the capture sequence, is connected at the start of the measurement. The solution with the enzyme substrate flows—delivered by the pump—first over the negative sample and then over the positive sample. The pAP formed by the enzyme is flushed away from the electrodes by the flow movement, so that the current is constant and low with the pump switched on. When the pump is now stopped, the pAP concentration increases with time owing to the enzyme activity. In the measurement, this is shown by a strong rise in the current signal by 20 nA/s. If the pump is switched on again, then this signal decreases back to the original value. This process may be repeated as many times as required.

FIG. 17 shows the current profile as a function of time with pump "on"/"off" in the described sensor arrangement with a positive and negative sample: the response curve 121 shows the profile of the pump current. A specific profile with individual peaks is obtained for the experiment, parameters being the activation of the pump on the one hand ("off"/"on") and the switchover of the measurement electrodes on the other hand. The measurement region of interest is respectively highlighted by shading. Switchover to the negative sample took place at t=400 s. Here, the current initially decreases when the pump is stopped, then remains constant for a short time and then increases slowly. This increase is caused by the diffusion of pAP from the positive sample to the negative sample. With the pump "on", a peak current is added to this since the electrolyte initially flows from the positive sample to the negative sample and therefore transports an increased pAP concentration to the neighboring electrode. Overall, the discrimination between positive and negative samples is very good.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV,* 358 F3d 870, 69 USPQ2d 1865 (Fed. Cir. 2004).

The invention claimed is:

1. A method for electrochemical detection of an analyte, comprising:

exposing the analyte to an enzyme attached to a substrate so that a hydrolytic cleavage process occurs between the enzyme and the substrate after which the enzyme is bound directly or indirectly to the analyte or displaced by the analyte, the enzyme having a post-cleavage concentration representing a concentration of the analyte;

converting the substrate and forming a reporter molecule during the hydrolytic cleavage process, the reporter molecule being capable of reverse electrochemical conversion under conditions in which the substrate is stable;

polarizing an electrode of a sensor during a measurement phase so that the reporter molecule is oxidized or reduced respectively to an oxidized form or a reduced form of the reporter molecule, the electrode being oppositely polarized during a relaxation phase so that the oxidized form or the reduced form of the reporter molecule is respectively reduced or oxidized at the electrode; and recording a current flowing to or from the electrode during the measurement phase to measure a concentration of the reporter molecule formed during the hydrolytic cleavage process.

2. The method as claimed in claim 1, wherein enzyme binds to the analyte.

3. The method as claimed in claim 1, wherein the reporter molecule is completely reduced or oxidized during the relaxation phase.

4. The method as claimed in claim 1, wherein toward an end of the measurement phase a capacitive current is small compared with a Faraday current.

5. The method as claimed in claim 4, wherein the reporter molecule is oxidized during the measurement phase and reduced toward an end of the relaxation phase.

6. The method as claimed in claim 4, wherein the reporter molecule is reduced during the measurement phase and oxidized toward an end of the relaxation phase.

7. The method as claimed in claim 6, wherein the electrode is polarized to potentials selected so that reduction and oxidation reactions of the reporter molecule take place in a diffusion limit current range.

8. The method as claimed in claim 6, wherein the measurement phase is repeated at a repetition rate of at least 0.5 Hz.

9. The method as claimed in claim 1, wherein the analyte has a marking element.

10. The method as claimed in claim 9, wherein the enzyme is an enzyme with a coupling element, which binds specifically to the marking element of the analyte.

11. The method as claimed in claim 10, wherein a capture molecule is immobilized on or in a vicinity of the electrode, the capture molecule binding specifically to the analyte.

12. The method as claimed in claim 11, wherein an auxiliary molecule is used, which contains a marking element that binds specifically to the capture molecule.

13. The method as claimed in claim 12, wherein the enzyme contains a coupling element, which binds specifically to the marking element of the auxiliary molecule.

14. The method as claimed in claim 11, wherein an auxiliary molecule is used which is coupled directly to the enzyme and binds specifically to the capture molecule.

15. The method as claimed in claim 14, wherein the auxiliary molecule is displaced by the analyte from its specific binding with the capture molecule.

16. The method as claimed in claim 14, wherein the analyte binds specifically to a capture molecule and the auxiliary molecule.

* * * * *